US006998369B2

(12) United States Patent
Hei et al.

(10) Patent No.: US 6,998,369 B2
(45) Date of Patent: Feb. 14, 2006

(54) ANTIMICROBIAL COMPOSITION

(75) Inventors: Robert D. P. Hei, Baldwin, WI (US); Guang-jong J. Wei, Mendota Heights, MN (US); David A. Halsrud, Mineapolis, MN (US); Kim R. Smith, Woodbury, MN (US); Teresa C. Podtburg, Waconia, MN (US)

(73) Assignee: Ecolab Inc., St. Paul, MN (US)

( * ) Notice: Subject to any disclaimer, the term of this patent is extended or adjusted under 35 U.S.C. 154(b) by 73 days.

(21) Appl. No.: 10/413,635

(22) Filed: Apr. 14, 2003

(65) Prior Publication Data

US 2003/0228996 A1 Dec. 11, 2003

Related U.S. Application Data

(60) Division of application No. 09/794,790, filed on Feb. 27, 2001, now Pat. No. 6,593,283, which is a continuation-in-part of application No. 09/560,170, filed on Apr. 28, 2000, and a continuation of application No. 09/641,775, filed on Aug. 18, 2000, now Pat. No. 6,544,942.

(51) Int. Cl.
*C11D 3/43* (2006.01)

(52) U.S. Cl. ....................... 510/111; 510/238; 510/423; 510/426; 510/434; 510/503; 510/504; 510/506

(58) Field of Classification Search ................ 514/557; 424/616, 405; 510/505, 407, 417, 506
See application file for complete search history.

(56) References Cited

U.S. PATENT DOCUMENTS

| | | | | |
|---|---|---|---|---|
| 3,867,300 A | | 2/1975 | Karabinos et al. | |
| 4,330,531 A | | 5/1982 | Alliger | |
| 4,414,128 A | | 11/1983 | Goffinet | |
| 4,592,787 A | | 6/1986 | Johnson | |
| 4,891,073 A | | 1/1990 | Shortt et al. | |
| 5,080,822 A | | 1/1992 | VanEanam | |
| 5,080,831 A | * | 1/1992 | VanEenam | 510/365 |
| 5,145,596 A | | 9/1992 | Blank et al. | |
| 5,158,710 A | | 10/1992 | VanEanam | |
| 5,180,749 A | | 1/1993 | Cusack et al. | |
| 5,230,821 A | * | 7/1993 | Larson et al. | 510/417 |
| 5,298,222 A | | 3/1994 | O'Leary | |
| 5,314,687 A | | 5/1994 | Oakes et al. | |
| 5,419,848 A | | 5/1995 | VanEanam | |
| 5,444,094 A | | 8/1995 | Malik et al. | |
| 5,529,887 A | | 6/1996 | Horn et al. | |
| 5,567,444 A | | 10/1996 | Hei et al. | |
| 5,585,341 A | | 12/1996 | Van Eanam | |
| 5,635,492 A | | 6/1997 | Corby | |
| 5,637,559 A | | 6/1997 | Koreltz et al. | |
| 5,674,538 A | | 10/1997 | Lokkesmoe et al. | |
| 5,744,440 A | | 4/1998 | Liu | |
| 5,786,319 A | | 7/1998 | Pedersen et al. | |
| 5,811,383 A | | 9/1998 | Klier et al. | |
| 5,849,682 A | | 12/1998 | Van Eanam | |
| 5,854,187 A | | 12/1998 | Blum et al. | |
| 5,900,256 A | | 5/1999 | Scoville et al. | |
| 5,922,665 A | | 7/1999 | Liu | |
| 5,972,874 A | | 10/1999 | Libutti et al. | |
| 5,977,042 A | | 11/1999 | Hernandez et al. | |
| 5,997,893 A | | 12/1999 | Jampani et al. | |
| 6,010,995 A | | 1/2000 | VanEanam | |
| 6,022,551 A | | 2/2000 | Jampani et al. | |
| 6,080,416 A | | 6/2000 | Jampani et al. | |
| 6,096,348 A | | 8/2000 | Miner et al. | |
| 6,274,542 B1 | * | 8/2001 | Carr et al. | 510/376 |
| 6,425,959 B1 | | 7/2002 | Man | |
| 6,506,261 B1 | | 1/2003 | Man | |
| 6,544,942 B1 | * | 4/2003 | Smith et al. | 510/417 |
| 6,593,283 B1 | * | 7/2003 | Hei et al. | 510/214 |
| 6,627,593 B1 | * | 9/2003 | Hei et al. | 510/375 |

FOREIGN PATENT DOCUMENTS

| | | |
|---|---|---|
| DE | 198 11 386 A1 | 9/1999 |
| EP | 0 414 309 A1 | 2/1991 |
| EP | 0 937 394 A1 | 8/1999 |
| FR | 2 761 080 A1 | 9/1998 |
| GB | 2 173 508 A | 10/1986 |
| WO | WO 83/00163 | 1/1983 |
| WO | WO 95/04459 | 2/1995 |
| WO | WO 97/18285 | 5/1997 |
| WO | WO 98/11168 | 3/1998 |
| WO | WO 99/41068 | 8/1999 |
| WO | WO 00/20518 | 4/2000 |

* cited by examiner

*Primary Examiner*—Gregory Webb
(74) *Attorney, Agent, or Firm*—IPLM Group, P.A.

(57) ABSTRACT

A method for antimicrobial treatment comprising applying to microbes a composition containing a diluting solvent (e.g., water), an antimicrobially-active solvent having a density different from the density of the diluting solvent, and an optional cosolvent, surfactant, or additional antimicrobial agent, wherein the amount of antimicrobially-active solvent or additional antimicrobial agent is sufficiently high and the amount of cosolvent or surfactant is sufficiently low so that the composition will provide greater than a 1-log order reduction in the population of bacteria or spores of *Bacillus cereus* within 10 seconds at 60° C. Preferred methods of the invention employ compositions containing an additional antimicrobial agent such as peroxyacetic acid. Compositions for use in the method can be prepared as concentrates, and used full strength or in diluted form.

18 Claims, No Drawings

ANTIMICROBIAL COMPOSITION

CROSS REFERENCE TO RELATED APPLICATION

This application is a divisional of application Ser. No. 09/794,790, filed Feb. 27, 2001, which is in turn a continuation-in-part of application Ser. No. 09/560,170, filed Apr. 28, 2000, and a continuation-in-part of application Ser. No. 09/641,775, filed Aug. 18, 2000 now U.S. Pat. No. 6,544,942.

TECHNICAL FIELD

This invention relates to compositions that can be used, for example, to clean, reduce the microbial population of, or sterilize surfaces, and to compositions that can be used for aseptic packaging.

BACKGROUND

There has been a longstanding need for antimicrobial agents having improved antimicrobial efficacy and improved speed of action. The specific requirements for such agents vary according to the intended application (e.g., sanitizer, disinfectant, sterilant, aseptic packaging treatment, etc.) and the applicable public health requirements. For example, as set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2), a sanitizer should provide a 99.999% reduction (5-log order reduction) within 30 seconds at room temperature, 25±2° C., against several test organisms.

Many antimicrobial agents (e.g., iodophors, peracids, hypochlorites, chlorine dioxide, ozone, etc.) have a broad spectrum of antimicrobial properties. However, these agents sometimes have inadequate activity against bacterial spores, fungal spores, and fungi. Killing, inactivating, or otherwise reducing the active population of bacterial spores and fungi on surfaces is particularly difficult. Bacterial spores have a unique chemical composition of spore layers that make them more resistant than vegetative bacteria to the antimicrobial effects of chemical and physical agents. Likewise, the unique chemical composition of fungal cells, especially mold spores, makes them more resistant to chemical and physical agents than are other microorganisms. This resistance can be particularly troublesome when the spores or fungi are located on surfaces such as food, food contact sites, ware, hospitals and veterinary facilities, surgical implements, and hospital and surgical linens and garments.

Control of the mold *Chaetomium funicola*, and of bacterial spore-forming microorganisms of the *Bacillus* species, can be especially important during food packaging, particularly during cold or hot aseptic filling of food and beverage products. Microorganisms of the *Bacillus* species include *Bacillus cereus, Bacillus mycoides, Bacillus subtilis, Bacillus anthracis,* and *Bacillus thuringiensis*. These latter microorganisms share many phenotypical properties, have a high level of chromosomal sequence similarity, and are known enterotoxin producers. *Bacillus cereus* is one of the most problematic because *Bacillus cereus* has been identified as possessing increased resistance to germicidal chemicals used to decontaminate environmental surfaces. For example, Blakistone et al., *Efficacy of Oxonia Active Against Selected Sporeformers*, Journal of Food Protection, Volume 62, pp.262–267, reported that *Bacillus cereus* was more tolerant to the effects of conventionally formulated peroxyacetic acid germicides than all other spore-forming bacteria tested, including other *Bacillus* and *Clostridium* species.

*Bacillus cereus* is frequently diagnosed as a cause of gastrointestinal disorders and has been suggested to be the cause of several food-borne illness outbreaks. Due to its rapid sporulating capacity, *Bacillus cereus* easily survives in the environment. *Bacillus cereus* is omnipresent in nature, and consequently can usually be found in animal feed and fodder. *Bacillus cereus* can contaminate raw milk via feces and soil, and can survive intestinal passage in cows and the pasteurization process.

*Bacillus cereus* is also known to cause serious human illness via environmental contamination. For example, *Bacillus cereus* is known to cause post-traumatic injury eye infections, which can result in visual impairment or loss of vision within 12–48 hours after infection. In addition, *Bacillus cereus* is regarded as transferable from washed surgical garments to patients.

Agents having greater or faster activity against bacterial spores, fungi, and other resistant microorganisms (particularly microorganisms of the *Bacillus* species) could help meet a substantial public health need, and one that is not adequately addressed by current commonly-used antimicrobial agents.

SUMMARY OF THE INVENTION

The present invention provides, in one aspect, a method for antimicrobial treatment comprising applying to microbes a composition containing a diluting solvent (e.g., water), an antimicrobially-active solvent having a density different from the density of the diluting solvent, and an optional cosolvent, surfactant, or additional antimicrobial agent, wherein the amount of antimicrobially-active solvent or additional antimicrobial agent is sufficiently high and the amount of cosolvent or surfactant is sufficiently low so that the composition will provide greater than a 1-log order reduction in the population of bacteria or spores of *Bacillus cereus* within 10 seconds at 60° C. In a preferred aspect, the methods of the invention provide broader spectrum antimicrobial action, providing greater than a 1-log order reduction within 10 seconds at 60° C. in one or more additional organisms such as the mold *Chaetomium funicola*. In a more preferred aspect, the methods of the invention provide greater than a 1-log order reduction within 10 seconds at 60° C. in *Chaetomium funicola, Bacillus subtilis* and *Bacillus cereus*.

In another aspect, the invention provides a method for antimicrobial treatment, comprising applying to microbes a composition as described above, wherein the composition further comprises such additional antimicrobial agent. In a particularly preferred embodiment, the additional antimicrobial agent comprises a peracid such as peroxyacetic acid; a peroxide such as hydrogen peroxide; or a halogen containing compound such as hypochlorous acid (or its salts), chlorine dioxide, hypobromous acid (or its salts), or an interhalide such as iodine monochloride, iodine dichloride, iodine tetrachloride, bromine chloride, iodine monobromide, or iodine dibromide.

In yet another aspect, the invention provides an antimicrobial concentrate and instructions for mixing the concentrate with water, wherein the concentrate comprises an antimicrobially-active solvent that has a density different from that of water, an optional cosolvent or surfactant, and an optional additional antimicrobial agent, the amounts of antimicrobially-active solvent and optional additional antimicrobial agent being. sufficiently high and the amount of cosolvent or surfactant being sufficiently low so that the composition will provide greater than a 1-log order reduction in the population of bacteria or spores of *Bacillus cereus* within 10 seconds at 60° C. In a particularly preferred embodiment, the composition comprises said additional antimicrobial agent and the amount of antimicrobially-active solvent is sufficiently high and the amount of cosolvent or surfactant is sufficiently low so that the composition does not form a clear single-phase solution or microemulsion when the concentrate is mixed with water according to the instructions.

In a further aspect, the invention provides an antimicrobial composition comprising a diluting solvent, an antimicrobially-active solvent having a density that is different from the density of the diluting solvent, an additional antimicrobial agent, and an optional cosolvent or surfactant, the amounts of antimicrobially-active solvent and of additional antimicrobial agent being sufficiently high and the amount of cosolvent or surfactant being sufficiently low so that the composition will provide greater than a 1-log order reduction in the population of bacteria or spores of *Bacillus cereus* or the mold *Chaetomium funicola* within 10 seconds at 60° C.

In yet another aspect, the invention provides an antimicrobial concentrate and instructions for mixing the concentrate with water, wherein the concentrate comprises an antimicrobially-active solvent that has a density different from that of water, an optional cosolvent or surfactant, and an additional antimicrobial agent, the amounts of antimicrobially-active solvent and additional antimicrobial agent being sufficiently high so that the composition will provide greater than a 1-log order reduction in the population of bacteria or spores of *Bacillus cereus* or the mold *Chaetomium funicola* within 10 seconds at 60° C. In a particularly preferred embodiment, the composition comprises a sufficiently high amount of additional antimicrobial agent and antimicrobially-active solvent such that the composition forms a clear single-phase solution when the concentrate is mixed with water according to the instructions, and provides greater than a 1-log order reduction in the population of bacteria or spores of *Bacillus cereus* or *Bacillus subtilis* and in the population of the mold *Chaetomium funicola* within 10 seconds at 60° C.

The method and compositions of the invention are especially useful for aseptic packaging, re-use clean-in-place (CIP) or clean-out-of-place (COP) systems, hospital disinfectants, veterinary clinic disinfectants, and as sporicides or sterilants.

DETAILED DESCRIPTION

As used in this invention, the term "sterilant" refers to a physical or chemical agent or process capable of destroying all forms of life (including bacteria, viruses, fungi, and spores) on inanimate surfaces. One procedure is described in *A.O.A.C. Sporicidal Activity of Disinfectants*, Official Methods of Analysis of the Association of Official Analytical Chemists, paragraph 966.04 and applicable sections, $15^{th}$ Edition, 1990 (EPA Guideline 91-2) As used in this invention, the term "antimicrobial composition" refers to a composition having the ability to cause greater than a 90% reduction (1-log order reduction) in the population of bacteria or spores of *Bacillus* species within 10 seconds at 60° C., using the above-mentioned *Germicidal and Detergent Sanitizing Action of Disinfectants* procedure. Preferably, *Bacillus cereus* or *Bacillus subtilis* are used in such procedure. Also preferably, the antimicrobial compositions of the invention provide greater than a 99% reduction (2-log order reduction), more preferably greater than a 99.99% reduction (4-log order reduction), and most preferably greater than a 99.999% reduction (5-log order reduction) in such population within 10 seconds at 60° C. Preferably, the antimicrobial compositions of the invention also provide greater than a 99% reduction (2-log order reduction), more preferably greater than a 99.99% reduction (4-log order reduction), and most preferably greater than a 99.999% reduction (5-log order reduction) in the population of one or more additional organisms such as the mold *Chaetomium funicola*. Because in their broadest sense these definitions for antimicrobial activity are different from some of the current governmental regulations, the use in connection with this invention of the term "antimicrobial" is not intended to indicate compliance with any particular governmental standard for antimicrobial activity.

As used in this invention, the term "sporicide" refers to a physical or chemical agent or process having the ability to cause greater than a 90% reduction (1-log order reduction) in the population of spores of *Bacillus cereus* or *Bacillus subtilis* within 10 seconds at 60° C. Preferably, the sporicidal compositions of the invention provide greater than a 99% reduction (2-log order reduction), more preferably greater than a 99.99% reduction (4-log order reduction), and most preferably greater than a 99.999% reduction (5-log order reduction) in such population within 10 seconds at 60° C.

As used in this invention, the term "sanitizer" refers to an agent that reduces the number of bacterial contaminants to safe levels as judged by public health requirements. Preferably, sanitizers for use in this invention will provide at least a 99.999% reduction (5-log order reduction) using the *Germicidal and Detergent Sanitizing Action of Disinfectants* procedure referred to above.

As used in this invention, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2).

As used in this invention, the term "preservative" refers to an agent that extends the storage life of food and non-food products by retarding or preventing deterioration of flavor, odor, color, texture, appearance, nutritive value, or safety. A preservative need not provide a lethal, irreversible action resulting in partial or complete microbial cell destruction or incapacitation. Sterilants, sanitizers, disinfectants, sporicides, viracides and tuberculocidal agents provide such an irreversible mode of action, sometimes referred to as "bactericidal" action. In contrast, a preservative can provide an inhibitory or bacteriostatic action that is reversible, in that the target microbes can resume multiplication if the preservative is removed. The principal differences between a preservative and a sanitizer primarily involve mode of action (a preservative prevents growth rather than killing microorganisms) and exposure time (a preservative has days to months to act whereas a sanitizer has at most a few minutes to act).

When applied to microbes (e.g., when applied to a surface containing microbes), the compositions of the invention exhibit antimicrobial action. The mechanism by which such action takes place is not completely understood. However, as shown in the Examples set out below, very rapid and substantially complete antimicrobial action can be attained.

Some preferred compositions and methods of the invention provide "pseudo-stabel" antimicrobial compositions that phase-separate following application of the composition to a surface. These compositions can also be described as exhibiting "phase-splitting" characteristics. The term "phase" refers to a homogeneous fluid portion that is present in or that can form in a fluid system. The term "phases" refers to the presence of more than one phase in a heterogeneous fluid system. The term "pseudo-stable" refers to a composition that forms a single phase when subjected to mild mixing or other agitation and retains that single phase for a sufficient period of time so that the composition can be applied to a surface, but which will promptly form two or more phases when left undisturbed. The term "phase-splitting" is meant to describe a single phase antimicrobially-active solvent-containing composition that forms at least two laminar phases promptly after being applied atop a generally horizontal surface or on a generally vertical surface, whereby a film containing a concentrated amount of the antimicrobially-active solvent lies between the surface and a film containing a much lower amount of the antimicrobially-active solvent. In a composition that has undergone phase splitting, the phase containing a concentrated amount of the antimicrobially-active solvent will be referred to as the solvent phase, and the phase containing a much lower amount of the antimicrobially-active solvent will be referred to as the dilute phase or diluting phase. For example, on counters, floors and other generally horizontal surfaces, the solvent phase will lie atop the surface (or atop microbes on the surface) and under the dilute phase or phases. On walls or other generally vertical surfaces, the solvent phase will lie adjacent the surface (or adjacent microbes on the surface) and under the dilute phase or phases. In such compositions, as is described in more detail below, attainment of pseudo-stable phase-splitting behavior can be achieved by employing a sufficiently high amount of antimicrobially-active solvent and a sufficiently low amount of cosolvent or surfactant.

In some compositions of the invention (and in some methods of the invention employing such compositions), the amount of antimicrobially-active solvent is sufficiently high and the amount of cosolvent or surfactant is sufficiently low so that the composition forms a "quasi-stable" antimicrobial composition. Such compositions have a clear or slightly cloudy appearance, do not form a clear single-phase solution or microemulsion, and do not undergo phase-splitting. However, they are antimicrobial compositions as defined herein. If in such quasi-stable compositions the amount of antimicrobially-active solvent is increased sufficiently, or if the amount of cosolvent or surfactant is decreased sufficiently, then these compositions will become pseudo-stable. Thus, these quasi-stable compositions almost exhibit pseudo-stable behavior, and will do so if modified as taught herein. As shown in some of the Examples set out below, these quasi-stable compositions can provide significant antimicrobial activity even though they do not undergo phase-splitting during use.

For simplicity, the remainder of this specification will discuss compositions that upon standing will form clear one-phase mixtures, cloudy two-phase dispersions or phase-splitting two-phase mixtures, it being understood that compositions forming three or more phases upon standing could be employed if desired.

The compositions of the invention can be formulated and sold for use as is, or as solvent concentrates. If desired, such concentrates can be used full-strength as antimicrobial agents. However, the concentrates typically will be diluted with a fluid (e.g., water) that subsequently forms the dilute phase. Preferably, the concentrate forms a single phase before such dilution and remains so while stored in the container in which it will be sold. When combined with water or other desired diluting fluid at an appropriate dilution level and subjected to mild agitation (e.g., by stirring or pumping the composition), some compositions of the invention will form a pseudo-stable dispersion, and other compositions of the invention will form a clear or quasi-stable solution or dispersion. If a pseudo-stable composition is formed, then the composition preferably remains in the pseudo-stable state for a sufficiently long period so that the composition can be applied to a surface before the onset of phase separation. The pseudo-stable state need only last for a few seconds when suitably rapid application techniques such as spraying are employed, or when agitation during application is employed. The pseudo-stable state desirably lasts for at least one minute or more after mixing and while the composition is stored in a suitable vessel, and preferably lasts for five minutes or more after mixing. Often normal refilling or replenishment of the applicator (e.g., by dipping the applicator in the composition) will provide sufficient agitation to preserve the pseudo-stable state of the composition during application.

Some of the highest observed levels of antimicrobial activity have been observed using pseudo-stable antimicrobial compositions of he invention. However, very high levels have also been observed for some clear or quasi-stable antimicrobial compositions of the invention. For some applications these clear or quasi-stable antimicrobial compositions solutions or dispersions will be preferred, as they require little or no mixing before or during use, and have a reduced tendency to separate during storage.

A variety of fluids can be used as the diluting solvent, including water in its liquid form; steam; condensed gases and other supercritical fluids (e.g., $CO_2$); perchloroethylene; oils such as silicone oils (e.g., siloxanes), gear oils, transaxle oils, mineral oils or vegetable oils; and carboxylic esters such as methyl soyate. Mixtures of diluting solvents can be used if desired. Especially useful oils include food grade or food-derived oils, flavorings, or fragrance oils. Preferably, the diluting solvent consists essentially of or consists of water in its liquid form. The remainder of this specification will primarily discuss the use of water in its liquid form as the diluting solvent, it being understood that other suitable fluids could be added to or substituted for water in its liquid form if desired.

The compositions of the invention can contain a variety of antimicrobially-active solvents. The antimicrobially-active solvent preferably is insoluble, or only sparingly soluble, in the diluting solvent. Thus for compositions containing water as the diluting solvent, and for concentrates intended to be diluted with water, the antimicrobially-active solvent preferably will have a water solubility less than about 5 wt. %, more preferably less than about 3 wt. %, and most preferably less than about 2 wt. %.

In general, the antimicrobially-active solvent is selected based upon the characteristics of the surface and microbes to which the antimicrobial composition will be applied and upon the nature of any coating, soil or other material that will be contacted by the antimicrobial composition and optionally removed from the surface. Polar solvents, and solvents that are capable of hydrogen bonding typically will perform well on a variety of surfaces and microbes and thus are preferred. Preferably, the antimicrobially-active solvent also has a high flashpoint (e.g., greater than about 30° C., more preferably greater than about 50° C., and most preferably greater than about 100° C.), low odor and low human and animal toxicity. Most preferably the antimicrobially-active solvent is a food-grade or cosmetic or flavorant additive.

Preferred antimicrobially-active solvents having a density different from that of water (and thus especially useful in compositions that will be diluted with water and applied atop horizontal or generally horizontal surfaces) include acetamidophenol (specific gravity 1.027); acetanilide (specific gravity 1.219; water solubility<1%); acetophenone (specific gravity 1.0238; water solubility<1%); [2-acetyl-1-methylpyrrole (specific gravity 1.04); benzyl acetate (specific gravity 1.0515; water solubility<1%); benzyl alcohol (specific gravity 1.0413; water solubility~4%); benzyl benzoate (specific gravity 1.118; water solubility<1%); benzyloxyethanol (specific gravity 1.07; water solubility<1%); t-butanol; ethers or hydroxyethers such as phenoxyethanol, phenoxyethanol-tetra ethoxylate, ethylene glycol phenyl ether (specific gravity 1.104; water solubility 2.3%; commercially available as DOWANOL EPH™ from Dow Chemical Co.) and propylene glycol phenyl ether (specific gravity 1.063; water solubility 1.1%; commercially available as DOWANOL PPH™ from Dow Chemical Co.); essential oils (e.g., benzaldehyde, pinenes (alphas, betas, etc.), terpineols, terpinenes, carvone, cinnamealdehyde, borneol and its esters, citrals, ionenes, jasmine oil, limonene, dipentene, linalool and its esters); dibasic esters such as dimethyl adipate, dimethyl succinate, dimethyl glutarate (often available in a mix with specific gravities greater than 1.00; including products available under the trade designations DBE, DBE-3, DBE-4, DBE-5, DBE-6, DBE-9, DBE-IB, and DBE-ME from DuPont Nylon), dimethyl malonate, diethyl adipate, diethyl succinate, diethyl glutarate, dibutyl succinate, and dibutyl glutarate; dialkyl carbonates such as dimethyl carbonate, diethyl carbonate, dipropyl carbonate, diisopropyl carbonate, and dibutyl carbonate; $C_{1-16}$ protonated carboxylic acids such as 2-ethyl-1-hexanoic acid, butyric acid, octanoic acid, heptanoic acid, nonanoic acid, and decanoic acid; $C_{1-12}$ organic anhydrides such as acetic anhydride, succinic anhydride, phthalic anhydride, maleic anhydride, and alkyl or alkenyl succinic anhydrides; organonitriles such as acetonitrile and benzonitrile; organo-phosphates and phosphonates such as tributyl phosphate, tripropyl phosphate, 2-ethyl-1-hexyl phosphate; and phthalate esters such as dibutyl phthalate, diethylhexyl phthalate, and diethyl phthalate. The water solubilities noted above are room temperature values. Benzyl alcohol, phenylethanol, essential oils, dibasic esters, dialkyl carbonates, ethylene glycol phenyl ether and propylene glycol phenyl ether are particularly preferred antimicrobially-active solvents. Mixtures of antimicrobially-active solvents can be used if desired.

The compositions of the invention should contain sufficient antimicrobially-active solvent to provide the desired rate and type of microbial reduction. Usually, antimicrobial concentrates of the invention will contain at least about 5 wt. % antimicrobially-active solvent, preferably at least about 25 wt. % antimicrobially-active solvent, more preferably at least about 65 wt. % antimicrobially-active solvent, and most preferably about 75 to about 95 wt. % antimicrobially-active solvent.

The compositions of the invention can contain one or more cosolvents or surfactants to assist in providing pseudo-stable or quasi-stable behavior. In general, cosolvents or surfactants that are present at concentrations below those at which single-phase coupling arises, or cosolvents or surfactants that are relatively inefficient or ineffective (with respect to their ability completely to solubilize or disperse the antimicrobially-active solvent in the diluting solvent and form a single-phase system), are preferred over cosolvents or surfactants that are present at higher concentrations or are more efficient or effective. This differs from the approach normally taken when formulating compositions containing cosolvents or surfactants. Normally, cosolvents and surfactants are selected for their ability to promote formation of stable single-phase solutions, microemulsions, or dispersions.

A variety of cosolvents can be employed. In general, the cosolvent is selected based upon the characteristics of the chosen antimicrobially-active solvent and the solubility of the chosen antimicrobially-active solvent in the diluting solvent. For compositions in which water serves as the diluting solvent, the cosolvent generally will have higher water solubility than the water solubility of the chosen solvent. Preferably, the cosolvent has a high flashpoint (e.g., greater than about 30° C., more preferably greater than about 50° C., and most preferably greater than about 100° C.), low odor and low human and animal toxicity.

Preferred cosolvents include 2-(2-aminoethoxy)ethanol, monoethanolamine, diethanolamine, triethanolamine, amyl acetate, amyl alcohol, butanol, 3-butoxyethyl-2-propanol, butyl acetate, n-butyl propionate, cyclohexanone, diacetone alcohol, diethoxyethanol, diethylene glycol methyl ether, diethylene glycol n-butyl ether, diisobutyl carbinol, diisobutyl ketone, dimethyl heptanol, dipropylene glycol n-butyl ether, dipropylene glycol methyl ether, dipropylene glycol propyl ether, dipropylene glycol tert-butyl ether, ethanol, ethyl acetate, 2-ethylhexanol, ethyl propionate, ethylene glycol butyl ether, ethylene glycol methyl ether acetate, hexanol, isobutanol, isobutyl acetate, isobutyl heptyl ketone, isophorone, isopropanol, isopropyl acetate, methanol, methyl amyl alcohol, methyl n-amyl ketone, 2-methyl-1-butanol, methyl ethyl ketone, methyl isobutyl ketone, 1-pentanol, n-pentyl propionate, 1-propanol, n-propyl acetate, n-propyl propionate, propylene glycol n-butyl ether, propylene glycol ethyl ether, propylene glycol methyl ether, propylene glycol n-propyl ether, tripropylene glycol methyl ether and tripropylene glycol n-butyl ether. Ethylene glycol butyl ether and dipropylene glycol n-butyl ether are particularly preferred cosolvents. Mixtures of cosolvents can be used if desired.

Commercially available cosolvents (all of which are available from Union Carbide Corp.) include Butoxyethyl PROPASOL™, Butyl CARBITOL™ acetate, Butyl CARBITOL™, Butyl CELLOSOLVE™ acetate, Butyl CELLOSOLVE™, Butyl DIPROPASOL™, Butyl PROPASOL™, CARBITOL™ PM-600, CARBITOL™ Low Gravity, CELLOSOLVE™ acetate, CELLOSOLVE™, Ester EEP™, FILMER IBT™, Hexyl CARBITOL™, Hexyl CELLOSOLVE™, Methyl CARBITOL™, Methyl CELLOSOLVE™ acetate, Methyl CELLOSOLVE™, Methyl DIPROPASOL™, Methyl PROPASOL™ acetate, Methyl PROPASOL™, Propyl CARBITOL™, Propyl CELLOSOLVE™, Propyl DIPROPASOL™ and Propyl PROPASOL™.

The compositions of the invention preferably should not contain excessive cosolvent, as the use of an excess of cosolvent will tend to cause formation of an antimicrobially inert single-phase solution or microemulsion. Instead, the amount of cosolvent preferably is just sufficient to provide the desired level of antimicrobial activity. Larger amounts of cosolvent may diminish the antimicrobial effectiveness of the compositions of the invention. Usually, antimicrobial concentrates of the invention will contain 0 to about 50 wt. % cosolvent, more preferably 0 to about 25 wt. % cosolvent, and most preferably 0 to about 20 wt. % cosolvent.

A variety of surfactants can be employed. In general, the surfactant identity and use level is selected based upon the characteristics of the chosen antimicrobially-active solvent and the solubility of the chosen antimicrobially-active solvent in the diluting solvent. For compositions in which water serves as the diluting solvent, the surfactant preferably will have an HLB value greater than or equal to about 13, or less than or equal to about 6. This value reflects the above-noted preference in the present invention for employing surfactants that are relatively inefficient or ineffective as emulsifiers. Preferably, the surfactant does not tend to cause formation of insoluble deposits, and has low odor and low toxicity. Mixtures of surfactants can be used if desired.

Preferred anionic surfactants include $C_6$–$C_{24}$ alkylbenzene sulfonates; $C_6$–$C_{24}$ olefin sulfonates; $C_6$–$C_{24}$ paraffin sulfonates; cumene sulfonate; xylene sulfonate; $C_6$–$C_{24}$ alkyl naphthalene sulfonates; $C_6$–$C_{24}$ alkyl or dialkyl diphenyl ether sulfonates or disulfonates, $C_4$–$C_{24}$ mono or dialkyl sulfosuccinates; sulfonated or sulfated fatty acids; $C_6$–$C_{24}$ alcohol sulfates (preferably $C_6$–$C_{12}$ alcohol sulfates); $C_6$–$C_{24}$ alcohol ether sulfates having 1 to about 20 ethylene oxide groups; and $C_4$–$C_{24}$ alkyl, aryl or alkaryl phosphate esters or their alkoxylated analogues having 1 to about 40 ethylene, propylene or butylene oxide units or mixtures thereof.

Preferred nonionic surfactants include $C_6$–$C_{24}$ alcohol ethoxylates (preferably $C_6$–$C_{14}$ alcohol ethoxylates) having 1 to about 20 ethylene oxide groups (preferably about 9 to about 20 ethylene oxide groups); $C_6$–$C_{24}$ alkylphenol ethoxylates (preferably $C_8$–$C_{10}$ alkylphenol ethoxylates) having 1 to about 100 ethylene oxide groups (preferably about 12 to about 20 ethylene oxide groups); $C_6$–$C_{24}$ alkylpolyglycosides (preferably $C_6$–$C_{20}$ alkylpolyglycosides) having 1 to about 20 glycoside groups (preferably about 9 to about 20 glycoside groups); $C_6$–$C_{24}$ fatty acid ester ethoxylates, propoxylates or glycerides; and C4–$C_{24}$ mono- or di-alkanolamides.

Preferred cationic surfactants include quaternary amine compounds having the formula:

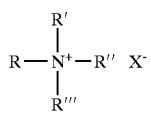

where R, R', R" and R'" are each a $C_1$–$C_{24}$ alkyl, aryl or aralkyl group that can optionally contain one or more P, O, S or N heteroatoms, and X is F, Cl, Br, I or an alkyl sulfate.

Preferred amphoteric surfactants include amine oxide compounds having the formula:

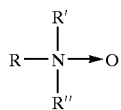

where R, R', R" and R'" are each a $C_1$–$C_{24}$ alkyl, aryl or aralkyl group that can optionally contain one or more P, O, S or N heteroatoms.

Another class of preferred amphoteric surfactants includes betaine compounds having the formula:

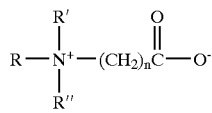

where R, R', R" and R'" are each a $C_1$–$C_{24}$ alkyl, aryl or aralkyl group that can optionally contain one or more P, O, S or N heteroatoms, and n is about 1 to about 10.

The antimicrobial compositions of the invention should not contain excessive amounts of surfactant, lest an antimicrobially inactive single-phase solution or microemulsion be formed. Instead, the amount of surfactant should be just sufficient to provide the desired level of antimicrobial activity. Larger amounts of surfactant may diminish the antimicrobial effectiveness of the compositions of the invention. Usually, the solvent concentrates of the invention will contain no more than about 10 wt. % surfactant, more preferably 0 to about 3 wt. % surfactant and most preferably 0 to about 1 wt. % surfactant. Most preferably, the concentrates are substantially surfactant-free.

The antimicrobial compositions of the invention preferably contain an additional antimicrobial agent. This additional antimicrobial agent can be dissolved or dispersed in the antimicrobially-active solvent or in the diluting solvent. Desirably, the additional antimicrobial agent will preferentially dissolve or disperse in the antimicrobially-active solvent rather than in the diluting solvent. Suitable additional antimicrobial agents include carboxylic acids, diacids, or triacids (e.g., butyric acid, heptanoic acid, octanoic acid, nonanoic acid, decanoic acid, salycic acid, mandelic acid, succinic acid, adipic acid, glutaric acid, EDTA and citric acid), carboxylic esters (e.g., p-hydroxy alkyl benzoates and alkyl cinnamates), sulfonic acids (e.g., dodecylbenzene sulfonic acid), iodo-compounds or active halogen compounds (e.g., iodine, interhalides, polyhalides, metal hypochlorites, hypochlorous acid, metal hypbromites, hypobromous acid, chloro- and bromo-hydantoins, chlorine dioxide and sodium chlorite), active oxygen compounds including hydrogen peroxide, isolated or equilibrium derived or isolated peracids such as chloroperbenzoic acids, peracetic acid, perheptanoic acid, peroctanoic acid, perdecanoic acid, performic acid, percitric acid, perglycolic acid, perlactic acid, perbenzoic acid, and monoester peracids derived from diacids or diesters (e.g., such as adipic, succinic, glutaric, or malonic acid and mixtures thereof), organic peroxides including benzoyl peroxide, alkyl benzoyl peroxides, ozone, singlet oxygen generators, and mixtures thereof, phenolic derivatives (e.g., o-phenyl phenol, o-benzyl-p-chlorophenol, tert-amyl phenol and $C_1$–$C_6$ alkyl hydroxy benzoates), quaternary ammonium compounds (e.g., alkyldimethylbenzyl ammonium chloride, dialkyldimethyl ammonium chloride and mixtures thereof), and mixtures of such antimicrobial agents, in an amount sufficient to provide the desired degree of microbial protection. Most of the aforementioned additional antimicrobial agents having about 1–6 carbons, or an ionic charge, would be mostly soluble in the diluting solvent; those with higher carbon numbers would generally be more soluble in the antimicrobially-active solvent. In either case, for a pseudo-stable antimicrobial composition it is preferred to use additional antimicrobial agents that can be drawn into the solvent phase or onto surfaces during phase separation.

Compositions of the invention containing such optional additional antimicrobial agents appear to have substantially greater antimicrobial effectiveness than comparison aqueous solutions or dispersions containing the additional antimicrobial agent alone. If present in the antimicrobial concentrates of the invention, the additional antimicrobial agent preferably is about 0.01 to about 30 wt. % of the concentrate, more preferably about 0.05 to about 10 wt. % and most preferably about 0.1 to about 5 wt. %.

If desired, the antimicrobial compositions of the invention can contain various adjuvants such as chelants, builders, thickeners, fragrances, dyes, pH adjusters, anticorrosion additives, antirust additives and indicators. The types and amounts of such adjuvants will be apparent to those skilled in the art.

The compositions of the invention can be formulated to include the diluting solvent (e.g., water) as sold, or the diluting solvent can be added at any time up to the time of use. Preferably, the concentrates of the invention contain little or no diluting solvent as sold. A variety of dilution ratios can be employed, so long as the diluted composition exhibits the desired antimicrobial behavior when applied to the target microbes. The ingredients in the concentrate can represent about 1 to about 99 wt. % of the diluted mixture, more preferably about 5 to about 50 wt. %, and most preferably about 6 to about 25 wt. %. The diluted antimicrobial compositions preferably contain about 0.01 to about 50 wt. % of the antimicrobially-active solvent, with concentrations of about 0.1 to 10 wt. % being more preferred and concentrations of about 0.5 to about 5 wt. % being most preferred. As a further guide, the diluted composition preferably contains antimicrobially-active solvent in an amount near the solubility limit of the antimicrobially-active solvent in the diluting solvent. In addition, the diluted antimicrobial compositions preferably are aqueous, contain additional antimicrobial agent, and are clear or quasi-stable.

The compositions of the invention can be sold in the form of a kit containing the composition together with suitable directions for carrying out the method of the invention. Such directions typically will include recommended dilution ratios, applications, application techniques and safety warnings.

Although no longer commercially available, an aqueous floor stripping agent concentrate previously sold in Canada as Fuller Formula 3100™ Super Concentrate (Fuller Brush, Québec) could be used as an antimicrobial composition of the invention. However, to do so the concentrate should be diluted at a ratio not recommended in the product instructions. Fuller Formula 3100™ Super Concentrate is believed to have contained about 49 wt. % benzyl alcohol, 17 wt. % monoethanolarnine, 10 wt. % sodium decyldiphenyl ether disulfonate and 24 wt. % water. Dilution of the concentrate at a 1:20 concentrate:water ratio was recommended on the product instructions. At that dilution ratio, the resulting mixture formed a stable single-phase solution. However, if diluted at a sufficiently larger concentrate:water ratio, the resulting mixture forms a quasi-stable or pseudo-stable composition. For example, at a 1:10 concentrate:water ratio, the composition is pseudo-stable and will undergo phase splitting when applied to a substrate and allowed to stand for a few minutes.

The antimicrobial compositions of the invention can be used for a variety of domestic or industrial applications, e.g., to reduce microbial or viral populations on a surface or object or in a body or stream of water. The compositions can be applied in a variety of areas including kitchens, bathrooms, factories, hospitals, dental offices and food plants, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials comprising, for example, ceramic, metal, glass, wood or hard plastic. Suitable soft surfaces include, for example paper; filter media, hospital and surgical linens and garments; soft-surface medical or surgical instruments and devices; and soft-surface packaging. Such soft surfaces can be made from a variety of materials comprising, for example, paper, fiber, woven or nonwoven fabric, soft plastics and elastomers. The compositions of the invention can also be applied to soft surfaces such as food and skin. The compositions are also suitable for application to growing or harvested plant material including leaves, stems, tubers, roots, seeds, and the like.

The antimicrobial compositions of the invention can be included in products such as sterilants, sanitizers, disinfectants, preservatives, deodorizers, antiseptics, fungicides, germicides, sporicides, virucides, detergents, bleaches, hard surface cleaners, hand soaps and pre- or post-surgical scrubs. The compositions have particular utility as cold or hot aseptic packaging treatments. The antimicrobial compositions can also be used in veterinary products such as mammalian skin treatments or in products for sanitizing or disinfecting animal enclosures, pens, watering stations, and veterinary treatment areas such as inspection tables and operation rooms.

The antimicrobial compositions of the invention can be used for treating skin diseases on animals (especially mammals), or those which spread via transfer to air or surface substrates, such as disease from fungi, molds, bacteria spores and viruses. These spreadable skin diseases include athletes foot fungus and hairy hoof wart disease, and the many organisms leading to Mastitis and other mammalian milking diseases. The disease can be a viral disease such as parvovirus, coxsackie virus, or herpes virus. The disease can also be bacterial, such as *S. aureus, E. coli, Streptococci*, etc., or a Mycobacterium type such as that leading to tuberculosis. The compositions may also be used to treat animal carcasses to reduce both pathogenic and non-pathogenic microbial levels.

The antimicrobial compositions can also be used on foods and plant species to reduce surface microbial populations; used at manufacturing or processing sites handling such foods and plant species; or used to treat process waters around such sites. For example, the compositions can be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compositions of the invention can be used to treat produce transport waters such as those found in flumes, pipe transports, cutters, slicers, blanchers, retort systems, washers, and the like.

The antimicrobial compositions have particular value for use on food packaging materials and equipment, and especially for cold or hot aseptic packaging. The compositions can also be used on or in ware wash machines, dishware, bottle washers, bottle chillers, warmers, third sink washers, cutting areas (e.g., water knives, slicers, cutters and saws) and egg washers. Particular foodstuffs that can be treated with compositions of the invention include eggs; meats, seeds, leaves, fruits and vegetables. Particular plant surfaces include both harvested and growing leaves, roots, seeds, skins or shells, stems, stalks, tubers, corms, fruit, and the like. Particular treatable surfaces include packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles.

The antimicrobial compositions can also be used on or in other industrial equipment and in other industrial process streams such as heaters, cooling towers, boilers, retort waters, rinse waters, aseptic packaging wash waters, and the like. The compositions can be used to treat microbes and odors in recreational waters such as in pools, spas, recreational flumes and water slides, fountains, and the like.

The antimicrobial compositions can also be used to reduce microbial and viral counts in air and liquids by incorporation into filtering media or breathing filters, e.g., to remove water and air-born pathogens such as *Legionella*.

Other hard surface cleaning applications for the antimicrobial compositions of the invention include clean-in-place systems (CIP), clean-out-of-place systems (COP), washer-decontaminators, sterilizers, textile laundry machines, ultra and nano-filtration systems and indoor air filters. COP systems can include readily accessible systems including wash tanks, soaking vessels, mop buckets, holding tanks, scrub sinks, vehicle parts washers, non-continuous batch washers and systems, and the like. CIP systems include a variety of devices that will be familiar to those skilled in the art, and will typically employ flow rates on the order of about 40 to about 600 liters per minute, temperatures from ambient up to about 70° C., and contact times of at least about 10 seconds, more preferably about 30 to about 120 seconds.

The antimicrobial compositions can be applied to microbes or to soiled or cleaned surfaces using a variety of methods. For example, the antimicrobial composition can be sprayed or wiped onto a surface; the composition can be caused to flow over the surface, or the surface can be dipped into the composition. The compositions can be formulated as liquids, gels, aerosols, waxes, solids, or powders. If steam or another gaseous diluting solvent is employed, then the compositions can be formulated to be applied in a gaseous state.

The invention is further illustrated in the following non-limiting examples, in which all parts and percentages are by weight unless otherwise indicated. In the examples the following procedures were employed:

EXAMPLE 1

Several compositions were evaluated by comparing them against a commercially available aseptic bottle washing biocide based on mixed peracids (MATRIXX™; Ecolab). Compositions containing only 1000 ppm or 2000 ppm of a single peracid or mixed peracids were used as controls. The remaining compositions were prepared by adding 10% of various solvents to an aqueous solution containing 1000 ppm or 2000 ppm of the mixed peracids. Non-solubilizing amounts of anionic surfactants were added to some of the compositions to affect minimal coupling and to yield, in some cases, pseudo-stable behavior and at least a partial phase-splitting condition. Addition of such non-stabilizing amounts tended to provide partial coupling and improved antimicrobial solution stability but not necessarily improved microbial control.

The compositions and controls were evaluated for antimicrobial activity using the procedure set out in set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2), using a 10 second contact time at 60° C. against the mold *Chaetomium funicola* (*C. funicola*). This brief contact time presented an especially challenging test, as evidenced by low observed log order reduction values for the controls.

Set out below in Table I are the run number, solvent, solvent description (in terms of its water solubility), peracid concentration, anionic surfactant concentration, appearance of the mixtures, after they had been allowed to stand for one minute, and observed log order reduction for *C. funicola*. The solvent description classified the solvents as highly soluble (>60% solubility in water), partially soluble (~20–60%), or sparingly soluble (<20%).

The compositions containing partially soluble solvents (Run Nos. 1-6 and 1-7) exhibited some phase-splitting behavior. The compositions containing sparingly soluble solvents (Run Nos. 1-8 through 1-11) exhibited substantial phase-splitting behavior. The results in Table I demonstrate that the addition of partially soluble and sparingly soluble solvents provided a substantial improvement in the antimicrobial efficacy of a commercial aseptic wash product, as can be seen by comparing control Run Nos. 1-1 through 1-3 to Run Nos. 1-6 through 1-11. The improved performance of Run Nos. 1-8 through 1-11 was especially dramatic, in that the observed activity improvement was 5 or more orders of magnitude compared to control Run Nos. 1-1 through 1-3. Use of highly soluble solvents (Run Nos. 1-4 and 1-5) provided only a small improvement in antimicrobial efficacy.

EXAMPLE 2

Several antimicrobial compositions of the present invention were evaluated for biocidal control, using the method of Example 1, and compared to several commercial products and to formulations from several U.S. patents. The comparison compositions formed clear (single-phase) formulations when prepared according to instructions. The compositions of the invention formed pseudo-stable cloudy compositions that underwent phase splitting following application. All tested compositions were evaluated against the spore-forming, enterotoxin producing pathogens *Bacillus cereus* and *Bacillus subtilis* and the mold *C. funicola* using a 10 second contact time at 60° C. Set out below in Table II are the run number, benzyl alcohol amount, amounts of additional ingredients, appearance of the mixtures, after they had been allowed to stand for one minute, and observed log order reduction for *B. cereus, Bacillus subtilis* and *C. funicola* for each composition.

TABLE I

| Run No. | Solvent | Solvent Description | Peracid Concentration | Anionic Surfactant Concentration | Appearance | *C. funicola* Log Reduction |
|---|---|---|---|---|---|---|
| I-1 | None | None | 2000 ppm[1] | 0.0% | clear | 0.1 |
| I-2 | None | None | 1000 ppm[2] | 0.26% | clear | 0.05 |
| I-3 | None | None | 2000 ppm[2] | 0.52% | clear | 0.1 |
| I-4 | Glycolic acid | highly soluble | 2000 ppm[2] | 0.62% | clear | 0.2 |
| I-5 | Dimethyl sulfoxide | highly soluble | 2000 ppm[2] | 0.62% | clear | 0.3 |
| I-6 | Hydrocarbon diol[3] | partially soluble | 2000 ppm[2] | 0.62% | slightly cloudy | 0.4 |
| I-7 | Propylene carbonate | partially soluble | 2000 ppm[2] | 0.62% | slightly cloudy | 1.6 |
| I-8 | Diester blend[4] | sparingly soluble | 2000 ppm[2] | 0.62% | very cloudy | 6.0 |
| I-9 | Diester blend[4] | sparingly soluble | 2000 ppm[1] | 0.0% | very cloudy | >4.4 |
| I-10 | Benzyl alcohol | sparingly soluble | 2000 ppm[2] | 0.62% | very cloudy | 5.0 |
| I-11 | Benzyl alcohol | sparingly soluble | 2000 ppm[1] | 0.0% | very cloudy | >4.7 |

[1]Peracetic acid from TSUNAMI ™ 100 (Ecolab)
[2]Peracid from MATRIXX ™, a commercial peracid (Ecolab)
[3]VARONIC ™ TD-I (Goldschmidt Chemical)
[4]DBE ™ (Dupont Nylon)

TABLE II

| Run No. | Benzyl Alcohol Amount | Additional Ingredient Amounts[1] | Appearance | B. cereus Log Reduction | B. subtilis Log Reduction | C. funicola Log Reduction |
|---|---|---|---|---|---|---|
| 2-1 | 5.0% | DBS[2] (0.1%) | clear (1-phase) | 0.2 | 0.0 | >4.4 |
| 2-2 | 2.0% | DBS[2] (0.1%) | clear (1-phase) | 0.1 | — | >4.4 |
| 2-3 | 2.0% | DBS[2] (5.0%) | clear (1-phase) | 0.0 | 0.2 | 0.3 |
| 2-4 | 2.0% | Nonionic surfactant[3] (5.0%) | clear (1-phase) | 0.0 | 0.1 | 0.4 |
| 2-5 | 0.0% | BUTYL CELLOSOLVE ™ (10.0%), DBS[2] (2.4%), anhydrous sodium merasilicate (2.0%)[4] | clear (1-phase) | 0.0 | 0.2 | 3.2 |
| 2-6 | 6.0% | DBS[2] (1.3%), ammonium hydroxide 28% (0.2%), Na-octane-1-sulfonate 40% (1.0%),[5] | clear (1-phase) | 0.0 | 0.1 | >4.8 |
| 2-7 | 4.0% | Ethanol (10%)[6] | clear (1-phase) | 0.05 | 0.1 | 4.6 |
| 2-8 | 2.0% | Ethanol (10%)[7] | clear (1-phase) | 0.1 | — | 4.7 |
| 2-9 | 4.0% | Glycerine (10%), DBS (2%) + other chemicals[8] | clear (1-phase) | 0.1 | 0.0 | 4.7 |
| 2-10 | 4.0% | Peracid[9] (0.1%), NAS[10] (0.24%) | cloudy (2-phase) | >6.3 | — | >4.4 |
| 2-11 | 3.5% | Peracid[11] (0.15%) | cloudy (2-phase) | >6.3 | — | >4.5 |
| 2-12 | 3.0% | Peracid[12] (0.1%), NAS[10] (0.24%) | cloudy (2-phase) | >6.3 | >6.7 | 3.8 |
| 2-13 | 3.0% | Peracid[9] (0.1%), NAS[10] (0.24%) | cloudy (2-phase) | >6.5 | >6.7 | 4.0 |
| 2-14 | 3.0% | Peracid[13] (0.1%) | cloudy (2-phase) | >6.2 | — | 3.4 |
| 2-15 | 0.0% | Diester blend[14] (5%) peracid[11] (0.1%), LAS (0.1%) | cloudy (2-phase) | 5.0 | — | >4.4 |
| 2-16 | 0.0% | Diester blend[14] (5%), $H_2O_2$ (2.1%)[15] | cloudy (2-phase) | — | 2.9 | >4.4 |
| 2-17 | 0.0% | Diester blend[14] (5%), $H_2O_2$ (2.1%)[15] | cloudy (2-phase) | — | >6.0 | >4.4 |
| 2-18 | 0.0% | Diester blend[14] (5%), NaOCl (0.02%)[16] | cloudy (2-phase) | 6.0 | >6.1 | >4.8 |
| 2-19 | 5.0% | NaOCl (0.02%)[16] | cloudy (2-phase) | — | — | >4.8 |
| 2-20 | 0.0% | Diester blend[14] (2.5%), NaOCl (0.025%)[17] | clear (1-phase) | >6.0 | >6.1 | >3.4 |

[1]The remainder or these compositions contained water
[2]DBS = dodecylbenzene sulfonate
[3]TERGITOL ™ 15-S-9 (Union Carbide)
[4]See Example 25 of U.S. Pat. No. 5,158,710
[5]See Example 10 of U.S. Pat. No. 5,849,682
[6]See Example 4 of U.S. Pat. No. 5,180,749
[7]See Example 1 of U.S. Pat. No. 5,180,749
[8]See Example 3 of U.S. Pat. No. 5,635,492, made with 0.1% "Rhamsan gum," 1% phosphate buffer and 0.003% blue dye.
[9]VORTEXX ™ or MATRIXX ™ commercial peracids (Ecolab)
[10]NAS = sodium, 1-octane sulfonate
[11]KX-6091 commercial peracid (Ecolab)
[12]15C commercial peracid (Ecolab)
[13]TSUNAMI-100 ™ commercial peracid (Ecolab)
[14]DBE-3 ™ (Dupont Nylon)
[15]Aged > 18 hrs
[16]Acidified to pH = 5.0 with acetic acid
[17]Acidified to pH = 6.0 with acetic acid Except as otherwise noted, the comparative compositions in Run Nos. 2-1 through 2-9 were prepared according to the listed examples of the cited patents or according to the mixing instructions of the cited commercial products. Each was found to yield a non-phase-splitting formulation. The compositions of the present invention in Run Nos. 2-10 through 2-19 yielded phase-splitting formulations that formed at least 2 phases. Run No. 2-20 yielded a pseudo-stable solution that was just slightly opaque but did not separate during the test time. The compositions of the invention exhibited significant antimicrobial efficacy against B. cereus, as well as broad-spectrum efficacy against B. subtilis and C. funicola. However, the composition of Run No. 2-19 underwent a chemical reaction and could not be employed at the desired active level against the Bacillus spores.

EXAMPLE 3

Using the method of Example 1, 5% portions of various sparingly soluble solvents were added to plain water or to commercial peracid bottle washing formulas (KX-6091, 15C, or VORTEXX™; Ecolab) and tested against the mold C. funicola using a 10 second contact time at 60° C. A non-emulsifying amount of the anionic surfactant sodium octene sulfonate was added to some of the compositions to slow down, but not prevent, phase-splitting. Set out below in Table III are the run number, solvent, peracid, peracid concentration, surfactant concentration, appearance of the mixtures after they had been allowed to stand for 1 minute, and observed log order reduction for *C. funicola* for each composition.

TABLE III

| Run No. | Solvent | Peracid | Peracid Concentration | Surfactant Concentration | Appearance | *C. funicola* Log Reduction |
|---|---|---|---|---|---|---|
| 3-1 | None | KX-6091[1] | 2000 ppm | 0 ppm | clear (1-phase) | 0.2 |
| 3-2 | None | 15C[1] | 2000 ppm | 2500 ppm | clear (1-phase) | 0.2 |
| 3-3 | None | VORTEXX[1] | 2000 ppm | 5960 ppm | clear (1-phase) | 0.1 |
| 3-4 | Glycol solvents[2] | KX-6091[1] | 2000 ppm | 0 ppm | cloudy (2-phase) | 1.3 |
| 3-5 | Glycol solvents[3] | KX-6091[1] | 2000 ppm | 0 ppm | cloudy (2-phase) | 3.7 |
| 3-6 | Glycol solvents[4] | KX-6091[1] | 2000 ppm | 0 ppm | cloudy (2-phase) | 3.2 |
| 3-7 | Diester blend[5] | KX-6091[1] | 2000 ppm | 1000 ppm[7] | cloudy (2-phase) | >4.4 |

TABLE III-continued

| Run No. | Solvent | Peracid | Peracid Concentration | Surfactant Concentration | Appearance | C. funicola Log Reduction |
|---|---|---|---|---|---|---|
| 3-8 | Glycol solvents[6] | None | 0 ppm | 1000 ppm[7] | cloudy (2-phase) | 2.8 |
| 3-9 | Glycol solvents[6] | KX-6091[1] | 1000 ppm | 1000 ppm[7] | cloudy (2-phase) | 4.3 |
| 3-10 | Glycol solvents[6] | KX-6091[1] | 2000 ppm | 1000 ppm[7] | cloudy (2-phase) | >4.4 |
| 3-11 | 2-ethyl-l-hexanol | KX-6091[1] | 2000 ppm | 1000 ppm[7] | cloudy (2-phase) | >4.2 |
| 3-12 | Dipentene | KX-6091[1] | 2000 ppm | 1000 ppm[7] | cloudy (2-phase) | 2.7 |
| 3-13 | Amyl acetate | KX-6091[1] | 2000 ppm | 1000 ppm[7] | cloudy (2-phase) | 3.3 |
| 3-14 | Benzyl alcohol | None | 0 ppm | 0 ppm | cloudy (2-phase) | >4.2 |
| 3-15 | Benzyl alcohol | KX-6091[1] | 2000 ppm | 0 ppm | cloudy (2-phase) | >4.2 |
| 3-16 | Tetrabutyl ammonium hydroxide[7] | 15C[1] | 2000 ppm | 2500 ppm | cloudy (2-phase) | 1.7 |
| 3-17 | Phenoxyethanol | 15C[1] | 2000 ppm | 2500 ppm | cloudy (2-phase) | 3.9 |
| 3-18 | Phenoxyethanol | VORTEXX[1] | 2000 ppm | 5960 ppm | cloudy (2-phase) | 4.8 |

[1]Commercial peracid (Ecolab)
[2]DOWANOL DPM ™ (Dow Chemical Co.)
[3]DOWANOL PPH ™ (Dow Chemical Co.)
[4]DOWANOL DPNP ™ (Dow Chemical Co.)
[5]DBE-3 ™ (Dupont Nylon)
[6]DOWANOL EPH ™ (Dow Chemical Co.)
[7]Neutralized to pH = 3.7 with acetic acid.

The compositions in Run Nos. 3-3 to 3-18 exhibited phase-splitting. The results in Table III demonstrate that substantial improvements in antimicrobial efficacy could be obtained by modifying all three commercial aseptic wash products, as can be seen by comparing control Run No. 3-1 with Run Nos. 3-4 through 3-7, 3-9 through 3-13 and 3-15; control Run No. 3-2 with Run Nos. 3-16 and 3-17; and control Run No. 3-3 with Run No. 3-18. Run Nos. 3-8 and 3-14 exhibited significant antimicrobial efficacy without an additional antimicrobial agent. A composition containing both a sparingly soluble antimicrobially-active solvent and an additional antimicrobial agent exhibited a synergistic improvement in performance compared to the use of either the antimicrobially-active solvent or the additional antimicrobial agent alone, as can be seen by comparing Run No. 3-10 with Run Nos. 3-1 and 3-8.

EXAMPLE 4

Using the method of Example 2, varying amounts of several sparingly soluble solvents were added to commercial peracid bottle washing formulations (TSUNAMI-100™, MATRIXX™, or KX-6091; Ecolab) and tested against the mold C. funicola using a 10 second contact time at 60° C. The surfactant dodecylbenzene sulfonate ("DBS") was added to some of the compositions to slow down, but not inhibit, phase-splitting. Set out below in Table IV are the run number, solvent, solvent concentration, peracid concentration, DBS concentration, appearance of the mixtures after they had been allowed to stand for 1 minute, and observed log order reduction for C. funicola for each composition.

TABLE IV

| Run No. | Solvent | Solvent (%) | Peracid (ppm) | DBS (ppm) | Appearance | C. funicola Log Reduction |
|---|---|---|---|---|---|---|
| 4-1 | Benzyl alcohol | 10% | 2000[1] | 1000 | cloudy (2-phase) | >4.4 |
| 4-2 | Benzyl alcohol | 10% | 2000[1] | 0 | cloudy (2-phase) | 3.9 |
| 4-3 | Benzyl alcohol | 5% | 2000[1] | 500 | cloudy (2-phase) | 4.1 |
| 4-4 | Benzyl alcohol | 1% | 2000[1] | 100 | clear (1-phase) | 0.1 |
| 4-5 | None | 0% | 2000[1] | 0 | clear (1-phase) | 0.1 |
| 4-6 | Diester blend[4] | 10% | 2000[2] | 1000 | cloudy (2-phase) | >4.4 |
| 4-7 | Diester blend[4] | 10% | 2000[2] | 0 | cloudy (2-phase) | >4.4 |
| 4-8 | Diester blend[4] | 5% | 2000[2] | 500 | cloudy (2-phase) | 4.2 |
| 4-9 | Diester blend[4] | 2.5% | 1500[2] | 0 | hazy (2-phase) | >4.4 |
| 4-10 | Diester blend[4] | 2.5% | 1200[2] | 0 | hazy (2-phase) | >4.4 |
| 4-11 | Diester blend[4] | 1% | 2000[2] | 100 | hazy (2-phase) | 1.2 |
| 4-12 | None | 0% | 2000[2] | 0 | clear (1-phase) | 0.2 |
| 4-13 | Diester blend[2] | 5% | 1000[3] | 1000 | cloudy (2-phase) | >4.4 |
| 4-14 | Diester blend[2] | 4% | 1000[3] | 0 | cloudy (2-phase) | >4.4 |
| 4-15 | Diester blend[2] | 3% | 1000[3] | 0 | cloudy (2-phase) | 3.2 |
| 4-16 | Diester blend[2] | 2% | 1000[3] | 0 | hazy (2-phase) | 3.1 |
| 4-17 | Diester blend[2] | 2.5% | 1500[7] | 0 | hazy (2-phase) | >4.4 |
| 4-18 | None | 0% | 1000[3] | 0 | clear (1-phase) | 0.05 |
| 4-19 | Solvent Mixture[5] | 5% | 2000[1] | 0 | cloudy (2-phase) | 3.6 |
| 4-20 | Solvent Mixture[5] | 1% | 2000[1] | 0 | clear (1-phase) | 0.6 |
| 4-21 | Phenoxyethanol | 5.0% | 2000[3] | 0 | cloudy (2-phase) | 4.8 |
| 4-22 | Phenoxyethanol | 5.0% | 2000[6] | 0 | cloudy (2-phase) | 3.9 |
| 4-23 | Phenoxyethanol | 2.5% | 1200[6] | 0 | hazy (2-phase) | 3.0 |
| 4-24 | Phenoxyethanol | 2.5% | 1500[6] | 0 | hazy (2-phase) | >4.0 |

TABLE IV-continued

| Run No. | Solvent | Solvent (%) | Peracid (ppm) | DBS (ppm) | Appearance | C. funicola Log Reduction |
|---|---|---|---|---|---|---|
| 4-25 | Phenylethanol | 3.0% | 2000[6] | 0 | cloudy (2-phase) | >4.5 |
| 4-26 | Tetrabutyl ammonium hydroxide, pH = 3.7 | 5.0% | 2000[6] | 0 | cloudy (2-phase) | >4.5 |

[1]TSUNAMI-100 ™ commercial peracid (Ecolab)
[2]DBE-3 ™ (Dupont Nylon)
[3]MATRIXX ™, mixed peracids (Ecolab)
[4]KX-6091 commercial peracid (Ecolab)
[5]Mixture containing 50% benzyl alcohol, 15% DOWANOL PPH ™ glycol solvent (Dow Chemical Co.), 15% BUTYLCARBITOL ™, 15% DOWANOL DPNB ™ glycol solvent (Dow Chemical Co.) and 5% SURFONIC 24-9 ™ nonionic surfactant (Huntsman Chemicals)
[6]15C commercial peracid (Ecolab)

For each of the antimicrobial compositions in Table IV, significant antimicrobial efficacy was obtained near, or just above, the solubility limit of the antimicrobially-active solvent in the diluting solvent. The results in Table IV show that substantial improvements in antimicrobial efficacy were obtained by modifying the commercial aseptic wash products, as can be seen by comparing control Run No. 4-5 with Run Nos. 4-1 through 4-3 and 4-19; control Run No. 4-12 with Run Nos. 4-6 through 4-11 and 4-22; and control Run No. 4-18 with Run Nos. 4-13 through 4-17. Compositions with and without added surfactant (DBS) exhibited increased antimicrobial activity, as can be seen, for example, from Run Nos. 4-1 through 4-3 and 4-6 through 4-11. Compositions containing mixtures of antimicrobially-active solvents are shown in Run Nos. 4-19 and 4-20.

EXAMPLE 5

Using the method of Example 2, varying amounts of benzyl alcohol were added to commercial peracid bottle washing formulations (KX-6091, 15C, TSUNAMI-100™, and VORTEXX™; Ecolab) and tested against the spore-forming, enterotoxin producing pathogen *Bacillus cereus* and the mold *C. funicola* using a 10 second contact time at 60° C. Set out below in Table V are the run number, solvent, solvent concentration, peracid concentration, appearance of the mixtures after they had been allowed to stand for 1 minute, and the observed log order reduction for *Bacillus cereus* and *C. funicola* for each composition.

TABLE V

| Run No. | Solvent | Solvent (%) | Peracid[1] (ppm) | Appearance | Log Reduction B. Cereus | Log Reduction C. funicola |
|---|---|---|---|---|---|---|
| 5-1 | None | 0% | 1000[1] | clear | 1.2 | 0.1 |
| 5-2 | None | 0% | 2000[1] | clear | 6.2 | 0.2 |
| 5-3 | None | 0% | 2000[2] | clear | — | 0.1 |
| 5-4 | None | 0% | 2000[3] | clear | 0.2 | 0.2 |
| 5-5 | None | 0% | 2000[4] | clear | 0.1 | 0.1 |
| 5-6 | Benzyl alcohol | 10% | 0 | very cloudy[5] | — | >4.4 |
| 5-7 | Benzyl alcohol | 10% | 1000[1] | very cloudy[5] | — | >4.4 |
| 5-8 | Benzyl alcohol | 4.5% | 0 | very cloudy[5] | 0.1 | >4.4 |
| 5-9 | Benzyl alcohol | 4.5% | 1000[1] | very cloudy[5] | 6.3 | >4.4 |
| 5-10 | Benzyl alcohol | 4.0% | 0 | very cloudy[6] | — | >4.4 |
| 5-11 | Benzyl alcohol | 4.0% | 1000[1] | very cloudy[6] | 3.6 | >4.4 |
| 5-12 | Benzyl alcohol | 4.0% | 1000[3] | very cloudy[6] | 4.8 | >4.4 |
| 5-13 | Benzyl alcohol | 3.5% | 0 | opaque[6] | — | 4.2 |
| 5-14 | Benzyl alcohol | 3.5% | 1000[1] | opaque[6] | 1.8 | >4.4 |
| 5-15 | Benzyl alcohol | 3.5% | 1000[2] + 1500[2] | clear | >6.3 | >4.4> |
| 5-16 | Benzyl alcohol | 3.5% | 2000[2] | clear | >6.3 | 4.5 |
| 5-17 | Benzyl alcohol | 3.5% | 1500[3] | clear | >6.3 | >4.5 |
| 5-18 | Benzyl alcohol | 3.5% | 0 | cloudy[5] | 3.4 | 2.6 |
| 5-19 | Benzyl alcohol | 3.0% | 1000[1] | clear | — | 2.7 |
| 5-20 | Benzyl alcohol | 3.0% | 1000[2] | clear | >6.5 | 3.8 |
| 5-21 | Benzyl alcohol | 3.0% | 2000[2] | clear | >6.3 | >4.7 |
| 5-22 | Benzyl alcohol | 3.0% | 2500[2] | clear | >6.3 | 4.5 |
| 5-23 | Benzyl alcohol | 3.0% | 1500[2] | clear | >6.3 | >4.5 |
| 5-24 | Benzyl alcohol | 3.0% | 1000[3] | clear | >6.5 | 4.3 |
| 5-25 | Benzyl alcohol | 3.0% | 1000[4] | cloudy[5] | >6.5 | 4.0 |
| 5-26 | Benzyl alcohol | 3.0% | 1000[1] | hazy | >6.2 | 4.0 |
| 5-27 | Benzyl alcohol | 2.5% | 1000[3] | clear | 6.4 | 4.2 |

TABLE V-continued

| Run No. | Solvent | Solvent (%) | Peracid[1] (ppm) | Appearance | Log Reduction B. Cereus | Log Reduction C. funicola |
|---|---|---|---|---|---|---|
| 5-28 | Benzyl alcohol | 2.5% | 1000[1] | cloudy[5] | 3.0 | 4.0 |
| 5-29 | Benzyl alcohol | 2.0% | 1000[3] | clear | 4.3 | 2.3 |
| 5-30 | Benzyl alcohol | 2.0% | 1000[2] | cloudy[5] | 4.7 | 4.0 |
| 5-31 | Benzyl alcohol | 2.0% | 1000[1] | clear | 3.7 | 3.8 |
| 5-32 | Benzyl alcohol | 1.5% | 1000[3] | clear | 5.9 | 1.2 |
| 5-33 | Benzyl alcohol | 1.5% | 0 | cloudy[5] | 0.05 | 0.2 |

[1]KX-6091 commercial peracid (Ecolab)
[2]15C commercial peracid (Ecolab)
[3]VORTEXX ™ commercial peracid (Ecolab)
[4]TSUNAMI-100 ™ commercial peracid (Ecolab)
[5]Rapid phase separation.
[6]Slow phase separation.

The results in Table V show substantial enhancement in antimicrobial efficacy for compositions both above and below the water solubility limit (as evidenced visually by solution clarity) of the antimicrobially-active solvent in the diluting solvent. Significant antimicrobial efficacy was also obtained against both organisms using some clear solutions (see, e.g., Run Nos. 5-15 through 5-17, 5-20 through 5-24, 5-27, 5-29, 5-31 and 5-32).

EXAMPLE 6

Aqueous mixtures containing 3% or 1% benzyl alcohol solvent and 2000 ppm or 1000 ppm of a commercial peracid bottle washing formulation (KX-6091 or VORTEXX™; Ecolab) were prepared. A surfactant was added to some of the mixtures. The mixtures were tested against the mold C. funicola using a 10 second contact time at 60° C. Set out below in Table VI are the run number, solvent concentration, peracid, surfactant, appearance of the mixtures after they had been all owed to stand for 1 minute , and the observed log order reduction for C. funicola for each composition.

The results in Table VI show that completely emulsifying the solvent system into a single phase using a surfactant can reduce antimicrobial efficacy, as can be seen by comparing Run Nos. 6-1 and 6-2. Conversely, use of a surfactant that can partially solubilize (or even destabilize) the composition can improve antimicrobial efficacy, as can be seen by comparing Run Nos. 6-3 and 6-4.

EXAMPLE 7

Using the method of Example 2, varying amounts of sparingly soluble solvent blends were added to a peracid bottle washing formulation (15C; Ecolab) and tested against spores of Bacillus subtilis and the mold C. funicola using a 10 second contact time at 60° C. Set out below in Table VII are the run number, solvents, solvent concentrations, peracid concentration, appearance of the mixtures after they had been allowed to stand for 1 minute, and the observed log order reduction for Bacillus cereus and C. funicola for each composition.

TABLE VI

| Run No. | Solvent, % | Peracid (ppm) | Surfactant | Appearance | C. funicola Log Reduction |
|---|---|---|---|---|---|
| 6-1 | (3%) | 2000 ppm[1] | None | cloudy, phase separating | 3.4 |
| 6-2 | (3%) | 2000 ppm[1] | mixed[2] | clear, 1-phase microemulsion | 0.2 |
| 6-3 | (1%) | 1000 ppm[3] | None | clear, 1-phase | 0.2 |
| 6-4 | (1%) | 1000 ppm | LAS-MIPA[4] | cloudy, phase separating | 2.8 |

[1]KX-6091 commercial peracid (Ecolab)
[2]1000 ppm of a mixture of 20% mineral oil, 40% alkyl polyglucoside, and 40% alcohol ethoxylate containing five ethylene oxide units.
[3]VORTEXX ™ commercial peracid (Ecolab)
[4]1000 ppm monoisopropanol amine salt of linear alkylbenzene sulfonate.

TABLE VII

| Run No. | Solvent(s) | Solvent (%) | Peracid[2] (ppm) | Appearance | Log Reduction B. subtilis | Log Reduction C. funicola |
|---|---|---|---|---|---|---|
| 7-1 | Diester blend[2] | 2.5% | 1500 | hazy | >6.5 | >4.4 |
| 7-2 | Benzyl alcohol | 3.5% | 1000 | hazy | 6.1 | 5.2 |
| 7-3 | Diester blend[2]/benzyl alcohol | 1.5/1.0% | 0 | clear | 0 | >4.4 |
| 7-4 | Diester blend[2]/benzyl alcohol | 1.0/1.5% | 0 | clear | 0 | >4.4 |
| 7-5 | Diester blend[2]/benzyl alcohol | 1.0/1.5% | 1500 | clear | >6.0 | >4.4 |
| 7-6 | Diester blend[2]/benzyl alcohol | 1.5/1.0% | 1500 | clear | >6.0 | >4.4 |

[1]15C commercial peracid (Ecolab)
[2]DBE-3 ™ (DuPont Nylon)

The results in Table VII show substantial enhancement in antimicrobial efficacy for compositions both above and below the water solubility limit (as evidenced visually by solution clarity) of the antimicrobially-active solvent. Most notable are the blended solvent systems shown in Run Nos. 7-5 and 7-6, which utilized each solvent below its solubility limit and a peracid, and provided significant broad-spectrum antimicrobial efficacy using clear solutions.

EXAMPLE 8

Using the method of Example 2, a sparingly soluble solvent was added to various additional antimicrobial agents and tested against *Bacillus cereus, Bacillus subtilis, C. funicola* and *N. fisheri* using a 10 second contact time at 60° C. Set out below in Table VIII are the run number, solvent and antimicrobial agent employed, solvent amount, antimicrobial agent amount, and the observed log order reduction for *Bacillus cereus, Bacillus cereus, C. funicola*, or *N. fisheri* for each composition.

The results in Table VIII illustrate use of various combinations of solvents and additional antimicrobial agents in the present invention. The mixture shown in Run No. 8-5 gave an especially synergistic result compared to the three control compositions of Run Nos. 8-6 through 8-8.

EXAMPLE 9

Using the method of Example 2, a composition was tested against the spore *Bacillus cereus* and the mold *C. funicola* using a 120 second contact time at 40° C. These experiments were run in order to determine the antimicrobial effectiveness of a composition of the present invention at a lower treatment temperature. Set out below in Table IX are the run number, solvent and additional antimicrobial agent, solvent amount, additional antimicrobial agent amount, and the observed log order reduction for *Bacillus cereus* and *C. funicola* for each composition.

TABLE VIII

| Run No. | Solvent + Additional Antimicrobial Agent(s) | Solvent Amount | Additional Agent Amount | Log Reduction B. cereus | Log Reduction B. subtilis | Log Reduction C. funicola | Log Reduction N. fisheri |
|---|---|---|---|---|---|---|---|
| 8-1 | Diester blend[1] + NaOCl[5] | 2.5% | 200 ppm | >6.3 | >6.0 | >4.4 | >4.6 |
| 8-2 | Diester blend[1] + NaOCl[5] | 2.5% | 400 ppm | — | >6.0 | >4.4 | — |
| 8-3[2] | Diester blend[1] + H$_2$O$_2$ | 5.0% | 2.1% | — | 2.9 | >4.4 | 2.1 |
| 8-4[2] | Diester blend[1] + H$_2$O$_2$ | 5.0% | .2% | — | >6.0 | >4.4 | — |
| 8-5 | Diester blend[1] + C$_8$FA[3] + POAA[4] | 2.5% | 800 + 1500 ppm | — | — | >4.8 | — |
| 8-6 | Diester blend[1] | 1.5% | 0 | — | — | 0.2 | — |
| 8-7 | C$_8$FA[3] | 800 ppm | 0 | — | — | 0.2 | — |
| 8-8 | POAA[4] | 1500 ppm | 0 | — | — | 0.2 | — |

[1]DBE-3 ™ (Dupont Nylon)
[2]The solution was aged >18 hours prior to use.
[3]C$_8$FA = octanoic acid.
[4]POAA = peroxyacetic acid.
[5]Acidified to pH = 6.0 with acetic acid.

TABLE IX

| Run No. | Solvent + Additional Antimicrobial Agent | Solvent (%) | Additional Agent Amount | Log Reduction B. cereus | Log Reduction C. funicola |
|---|---|---|---|---|---|
| 9-1 | Diester blend[1] + NaOCl | 2.5% | 200 ppm | >6.3 | 3.2 |
| 9-2[2] | Diester blend[1] + H$_2$O$_2$ | 3.0% | 0.84% | >6.3 | 1.0 |
| 9-3[2] | Diester blend[1] + H$_2$O$_2$ | 2.5% | .70% | >6.3 | 1.0 |
| 9-4 | Diester blend[1] + POAA[3] | 2.5% | 1500 ppm | >6.3 | 2.7 |

[1]DBE-3 ™ (Dupont Nylon)
[2]The solution was aged >18 hours prior to use.
[3]Peroxyacetic acid The results in Table IX demonstrate the ability to induce effective microbial control at lower treatment temperatures.

EXAMPLE 10

Aqueous mixtures containing an antimicrobially-active solvent, a peracid, or mixtures of both were prepared and evaluated against the spore-forming, enterotoxin producing pathogen *Bacillus cereus* using a 10 second contact time at 60° C. Set out below in Table X are the run number, solvent, solvent concentration, peracid concentration, and the observed log order reduction for *B. cereus* for each composition.

TABLE X

| Run No. | Solvent | Solvent, (wt %) | Peracid (ppm) | B. cereus Lo2 Reduction |
|---|---|---|---|---|
| 10-1 | None | 0% | 1000[1] | 0.2 |
| 10-2 | None | 0% | 3000[1] | 0.9 |
| 10-3 | None | 0% | 4000[2] | 0.8 |
| 10-4 | Benzyl alcohol | 3% | 0 | 0.1 |
| 10-5 | Benzyl alcohol | 3% | 1000[1] | 2.4 |
| 10-6 | Diester blend[3] | 3% | 0 | 0.3 |
| 10-7 | Diester blend[3] | 3% | 1000[2] | 3.6 |
| 10-8 | Diester blend[3] | 2.5% | 1500[4] | >6.3 |

[1]OXONIA ACTIVE ™ commercial peracid (Ecolab)
[2]MATRIXX ™ commercial peracid (Ecolab)
[3]15C commercial peracid (Ecolab)
[4]DBE-3 ™ (Dupont Nylon)

The results in Table X show the substantial synergistic improvements in sporicidal efficacy that tan be obtained by combining the antimicrobially-active solvent and a peracid, as can be seen by comparing Run Nos. 10-1, 10-4 and 10-5, and Run Nos. 10-3, 10-6 and 10-7. Run No. 10-7 provided nearly a 3-log reduction improvement compared to the use of the antimicrobially-active solvent or peracid alone, while using a lower quantity of peracid. Run No. 10-8 provided an especially effective sporicide at even lower levels of antimicrobially-active solvent and peracid.

EXAMPLE 11

Using the method of Example 10, aqueous mixtures containing 3% benzyl alcohol, or varying amounts of several peracids (KX-6091, MATRIXX™, TSUNAMI 100™ or OXONIA ACTIVE™; Ecolab), or mixtures of both benzyl alcohol and peracid were prepared and evaluated as possible sterilant formulations against the spore-forming, enterotoxin producing pathogen *Bacillus cereus* using a 10 second contact time at 60° C. Set out below in Table VIII are the run number, solvent, peracid concentration, and the observed log order reduction for *B. cereus* for each composition.

TABLE XI

| Run No. | Solvent | Solvent, (wt %) | Peracid, (ppm) | B. cereus Log Reduction |
|---|---|---|---|---|
| 11-1 | Benzyl alcohol | 3% | 1000[1] | >6.5 |
| 11-2 | Benzyl alcohol | 3% | 1000[2] | >6.5 |
| 11-3 | Benzyl alcohol | 3% | 1000[3] | >5.6 |
| 11-4 | Benzyl alcohol | 3% | 1000[4] | 2.4 |
| 11-5 | Benzyl alcohol | 3% | 1000[5] | >6.3 |
| 11-5 | Benzyl alcohol | 3% | None | 0.1 |
| 11-6 | None | 0% | 4000[4] | 0.8 |
| 11-7 | None | 0% | 4000[2] | 0.8 |

[1]KX-6091 commercial peracid (Ecolab)
[2]MATRIXX ™, mixed peracid (Ecolab)
[3]TSUNAMI-100 ™ commercial peracid (Ecolab)
[4]OXONIA ACTIVE ™ commercial peracid (Ecolab)
[5]15C commercial peracid (Ecolab)

The results in Table XI show the substantial synergistic improvements in sporicidal efficacy that can be obtained by combining the antimicrobially-active solvent and a peracid. For example, Run No. 11-2 provided more than a 6-log reduction improvement compared to the use of the antimicrobially-active solvent alone (Run No. 11-5), and nearly a 6-log reduction improvement compared to the use of the peracid alone (Run No. 11-7), yet required only one-fourth as much peracid.

EXAMPLE 12

Using the method of Example 10, aqueous mixtures containing various solvents and varying amounts of a peracid (15C; Ecolab) were prepared and evaluated against the spore-forming, enterotoxin producing pathogen *Bacillus cereus* using a 10 second contact time at 60° C. Set out below in Table XII are the run number, solvent type and concentration, peracid type and concentration, and the observed log order reduction for *B. cereus* for each composition. As shown, a wide range of chemical solvent classes yielded substantial spore reductions.

TABLE XII

| Run No. | Solvent Type and Amount (wt %) | Peracid Type and Amount (ppm) | B. cereus Log Reduction |
|---|---|---|---|
| 12-1 | Phenoxyethanol (2.5%) | 15C[1] (1200 ppm) | 3.4 |
| 12-2 | Phenethanol (3.0%) | 15C[1] (2000 ppm) | >6.4 |
| 12-3 | Benzoic acid (0.5%) | 15C[1] (2000 ppm) | >6.0 |
| 12-4 | Benzyl benzoate (0.5%) | 15C[1] (2000 ppm) | 2.3 |
| 12-5 | Diester blend[2] (2.5%) | 15C[1] (1200 ppm) | >6.2 |

[1]15C commercial peracid (Ecolab)
[2]DBE-3 ™ (Dupont Nylon)

EXAMPLE 13

Using the method of Example 10, aqueous mixtures containing varying types and amounts of solvents and varying types and amounts of several peracids were prepared and evaluated as sporicides against *Bacillus subtilis*, using a 10 second contact time at 60° C. Set out below in Table XIII are the run number, solvent, solvent concentration, peracid type and concentration, and the observed log order reduction for *B. subtilis* for each composition.

TABLE XIII

| Run No. | Solvent | Solvent wt % | Peracid Type and Amount, ppm | *B. subtilis* Log Reduction |
|---|---|---|---|---|
| 13-1 | Benzyl alcohol | 3.0% | VORTEXX [TM,1] (1000 ppm) | >6.7 |
| 13-2 | Benzyl alcohol | 3.0% | VORTEXX [TM,1] (1500 ppm) | >6.7 |
| 13-3 | Benzyl alcohol | 3.5% | VORTEXX [TM,1] (1000 ppm) | >6.7 |
| 13-4 | Benzyl alcohol | 3.0% | VORTEXX [TM,1] (1500 ppm) | >6.7 |
| 13-5 | Benzyl alcohol | 3.5% | 15C[2] (1000 ppm) | 5.6 |
| 13-6 | Benzyl alcohol | 2.5% | VORTEXX [TM,1] (1500 ppm) | >6.7 |
| 13-7 | Benzyl alcohol | 2.0% | VORTEXX [TM,1] (1500 ppm) | >6.7 |
| 13-8[4] | Benzyl alcohol | 2.0% | TSUNAMI 100 [TM,3] (1000 ppm) | >6.7 |
| 13-9 | Phenoxyethanol | 5.0% | 15C[2] (1000 ppm) | 6.7 |
| 13-10 | Phenoxyethanol | 5.0% | VORTEXX [TM,1] (1000 ppm) | 6.7 |
| 13-11 | Phenoxyerhanol | 2.5% | 15C[2] (1500 ppm) | >6.5 |
| 13-12 | Phenoxyethanol-tetra ethoxylate | 5.0% | 15C[2] (1000 ppm) | 6.7 |
| 13-13 | Diester blend[5] | 2.5% | 15C[2] (1500 ppm) | >6.5 |
| 13-14 | Diester blend[5] | 1.5% | VORTEXX [TM,1] (1500 ppm) | >6.7 |
| 13-15 | Tert-butanol | 5.0% | VORTEXX [TM,1] (1500 ppm) | >6.7 |

[1]VORTEXX ™, mixed peracid (Ecolab)
[2]15C commercial peracid (Ecolab)
[3]TSUNAMI 100 ™, commercial peracid (Ecolab)
[4]Also contained 1000 ppm sodium octyl sulfonate
[5]DBE-3 ™ (Dupont Nylon)

EXAMPLE 14

Using the method of Example 2, aqueous mixtures containing 2.5 wt.% DBE-3™ solvent (diester blend, DuPont Nylon) and a peracid were prepared and evaluated as a general antimicrobial agent against *S. aureus*, *E. coli*, or *N. fisheri* using a 10 second contact time at 60° C. Set out below in Table XIV are the run number, peracid type and amount, and the observed log order reduction for each organism.

TABLE XIV

| Run No. | Peracid Type and Amount (ppm) | Log Reduction | | |
|---|---|---|---|---|
| | | *S. aureus* | *E. coli* | *N. fisheri* |
| 14-1 | 15C[1] (2000 ppm) | — | — | 3.7 |
| 14-2 | OXONIA ACTIVE [TM,2] (75 ppm) | >7.2 | >7.1 | — |

[1]Commercial peracid (Ecolab)
[2]Commercial peracid (Ecolab)

Various modifications and alterations of this invention will be apparent to those skilled in the art without departing from the scope and spirit of this invention. It should be understood that this invention is not limited to the illustrative embodiments set forth above.

We claim:

1. A method for antimicrobial treatment comprising applying to microbes a composition containing a diluting solvent; an antimicrobially-active solvent having a density different from the density of the diluting solvent and comprising butyl alcohol, t-butanol, ether, hydroxyether, dibasic ester or $C_{1-16}$ protonated carboxylic acid; an additional antimicrobial agent comprising chloroperbenzoic acid, peracetic acid, perheptanoic acid, peroctanoic acid, perdecanoic acid, performic acid, percitric acid, perglycolic acid, perlactic acid, or perbenzoic acid; and an optional cosolvent or surfactant; wherein the amounts of antimicrobially-active solvent and additional antimicrobial agent are sufficiently high and the amount of cosolvent or surfactant is sufficiently low so that the treatment will provide greater than a 1-log order reduction in a population of *Bacillus cereus* within 10 seconds at 60° C.

2. A method according to claim 1 wherein the dilating solvent comprises water.

3. A method according to claim 1 wherein the additional antimicrobial agent comprises peracetic acid.

4. A method according to claim 1 wherein the additional antimicrobial agent comprises peroctanoic acid.

5. A method according to claim 1 wherein the composition will also provide greater than a 1-log order reduction in a population of *Chaetomium funicola* within 10 seconds at 60° C.

6. A method according to claim 1 wherein the treatment comprises applying the composition to a hard surfrce, soft surface, porous surface, food substance or skin.

7. A method according to claim 1 wherein the treatment comprises applying the composition to food packaging and the composition will provide greater than a 3-log order reduction in the population of *Bacillus cereus* within 10 seconds at 60° C.

8. A method according to claim 7 wherein the food packaging is aseptic food packaging.

9. A method according to claim 1 wherein the treatment comprises applying the composition to hospital or surgical linens or garments and wherein the composition will provide greater than a 3-log order reduction in the population of *Bacillus cereus* within 10 seconds at 60° C.

10. A method according to claim 1 wherein the treatment comprises sanitizing a solution or hard surface and wherein the composition will provide greater than a 3-log order reduction within 10 seconds at 60° C. in the population of the *Bacillus* species in such solution or on such surface.

11. A method according to claim 1 wherein the treatment comprises disinfecting a hard surface and wherein the composition will provide greater than a 5-log order reduction within 10 seconds at 60° C. in the population of the *Bacillus* species on such surface.

12. A method according to claim 1 wherein the treatment acts as a sporicide in a solution or on a bard surface and wherein the composition will provide greater than a 5-log order reduction within 10 seconds at 60° C. in the population of the *Bacillus* species in such solution or on such surface.

13. A method according to claim 1 wherein the treatment comprises sterilizing a surface and wherein the composition will provide substantially complete elimination of the *Bacillus* species on such surface.

14. A method according to claim 1 wherein the treatment comprises reducing microbial or viral populations on a surface or object or in a body or stream of water.

15. A method according to claim 1 wherein the treatment comprises a teat dip, hard surface cleaner, sanitizer, disinfectant, sterilizer, surgical garment treatment, ware wash, wash water treatment, bleach, laundry liquid, plant treatment or food treatment.

16. A method according to claim 1 wherein the antimicrobially-active solvent comprises a $C_{1-16}$ protonated carboxylic acid.

17. A method according to claim 1 wherein the antimicrobially-active solvent comprises a dibasic ester.

18. A method according to claim 17 wherein the dibasic ester is at least one or more of dimethyl adipate, dimethyl succinate, dimethyl glutarate, diethyl adipate, diethyl succinate, diethyl glutarate, dibutyl succinate or dibutyl glutarate.

* * * * *

UNITED STATES PATENT AND TRADEMARK OFFICE
CERTIFICATE OF CORRECTION

PATENT NO. : 6,998,369 B2
APPLICATION NO. : 10/413635
DATED : February 14, 2006
INVENTOR(S) : Hei et al.

It is certified that error appears in the above-identified patent and that said Letters Patent is hereby corrected as shown below:

<u>Title page, item [75] Inventors</u>
"Mineapolis" should read --Minneapolis--

<u>Title page, item [60] Related U.S. Application Data</u>
"continuation" should read --continuation-in-part--

<u>Column 1</u>
Line 7, After "2001," insert --now U.S. Patent 6,593,283--

<u>Column 3</u>
Line 52, After "2)" insert --.-- and then "As used..." should begin a new paragraph <u>Column 6</u>
Line 11, "he" should read --the--

<u>Column 9</u>
Line 14, "C4 should read --$C_4$--

<u>Column 13</u>
Table 1, under Run No., "I" should read --1--

<u>Column 21</u>
Line 42, "all owed" should read --allowed--

<u>Column 25</u>
Line 31, in the header for Table X, "Lo2" should read --Log--

UNITED STATES PATENT AND TRADEMARK OFFICE
CERTIFICATE OF CORRECTION

PATENT NO. : 6,998,369 B2
APPLICATION NO. : 10/413635
DATED : February 14, 2006
INVENTOR(S) : Hei et al.

It is certified that error appears in the above-identified patent and that said Letters Patent is hereby corrected as shown below:

Column 25
Line 46, "tan" should read --can--

Signed and Sealed this

Seventh Day of August, 2007

JON W. DUDAS
*Director of the United States Patent and Trademark Office*